(12) United States Patent
Cho et al.

(10) Patent No.: US 6,734,290 B2
(45) Date of Patent: May 11, 2004

(54) DYES AND METHODS OF PREPARING THEM

(75) Inventors: Sung Yong Cho, Seoul (KR); Tae Chung Kang, Goyang-si (KR); Woo Jin Yoon, Seoul (KR); Sang Ki Yang, Seoul (KR); Sung Il Myung, Seoul (KR); Ho Lee, Seoul (KR)

(73) Assignee: Kyung-In Synthetic Corporation, Seoul (KR)

( * ) Notice: Subject to any disclaimer, the term of this patent is extended or adjusted under 35 U.S.C. 154(b) by 0 days.

(21) Appl. No.: 10/449,810

(22) Filed: May 29, 2003

(65) Prior Publication Data

US 2004/0024189 A1 Feb. 5, 2004

(30) Foreign Application Priority Data

| May 30, 2002 | (KR) | 10-2002-0030333 |
| May 30, 2002 | (KR) | 10-2002-0030398 |
| May 30, 2002 | (KR) | 10-2002-0030331 |

(51) Int. Cl.[7] ............ C09B 62/01; D06P 1/38; C07C 309/46
(52) U.S. Cl. ............ 534/635; 534/612; 534/636; 534/637; 534/642; 562/58; 8/549
(58) Field of Search ............ 534/612, 635–637, 534/642; 562/58; 8/549

(56) References Cited

U.S. PATENT DOCUMENTS

| 4,997,919 A | 3/1991 | Schaulin | 534/637 |
| 5,117,050 A * | 5/1992 | Pandl et al. | 562/58 |
| 5,484,899 A | 1/1996 | Deitz et al. | 534/618 |
| 5,548,071 A | 8/1996 | Deitz et al. | 534/612 |

FOREIGN PATENT DOCUMENTS

| EP | 0 623 655 A1 | 11/1994 |
| FR | 1 177 851 | 4/1959 |
| WO | 03/040239 A1 | 3/2003 |

* cited by examiner

*Primary Examiner*—Fiona T. Powers
(74) *Attorney, Agent, or Firm*—Ladas & Parry

(57) ABSTRACT

The present writing relates to a novel fiber-reactive dye of the formula

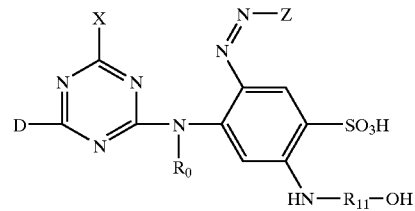

wherein $R_{11}$, D, $R_0$, X and Z are as defined in the specification. The novel dye according to the present writing can be used in dyeing and printing fibre materials, especially, cellulosic fibre materials by a general fixing method, and a good adsorbing/fixing rate and an excellent fastness to light and wet treatment.

8 Claims, 2 Drawing Sheets

DYES AND METHODS OF PREPARING THEM

TECHNICAL FIELD

The present writing relates to fiber-reactive dyes, which have two heterogeneous monoazo dye radical moieties in the chemical structure thereof, and methods of preparing them.

BACKGROUND

Fiber-reactive dyes with two monoazo dye radical moieties in the molecular structure have been disclosed in U.S. Pat. No. 5,484,899 and U.S. Pat. No. 5,548,071.

The dyes according to the present writing are distinguished by an excellent fixing capacity and good wet- and light-fastness properties. Accordingly, the dyes according to this writing can solve problems occurring upon dying fibre materials at a high concentration with C.I. Reactive Red 120 compound and C.I. Reactive Yellow 84 compound, being monochlorotriazine-based reactive dyes, and with C.I. Reactive Red 195 compound and C.I. Reactive Yellow 145 compound, being difunctional reactive dyes, of which the structures are illustrated below, respectively.

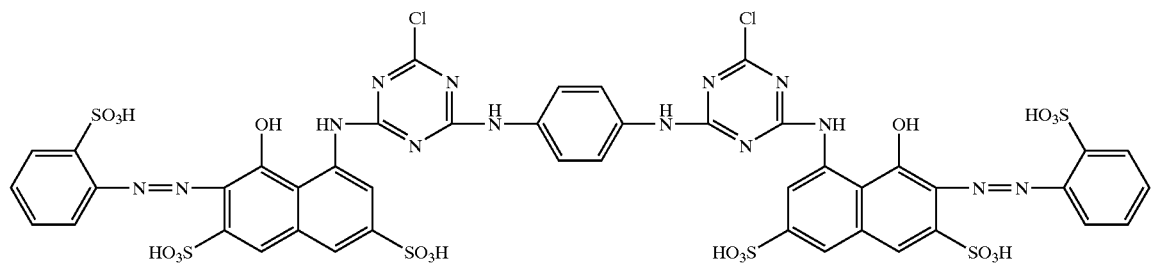

C.I. Reactive Red 120

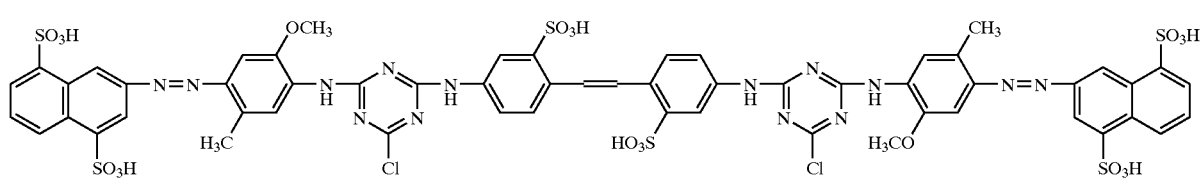

C.I. Reactive Yellow 84

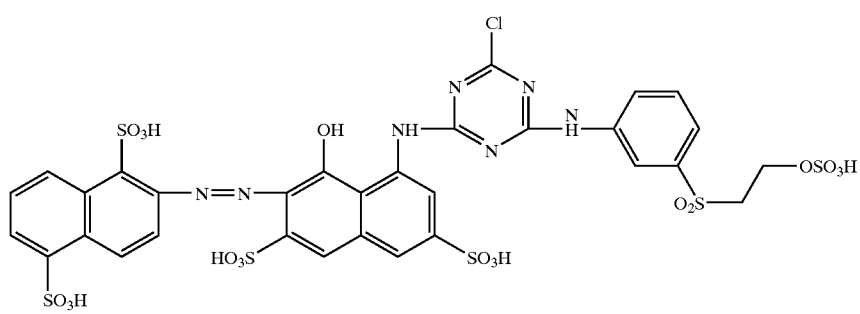

C.I. Reactive Red 195

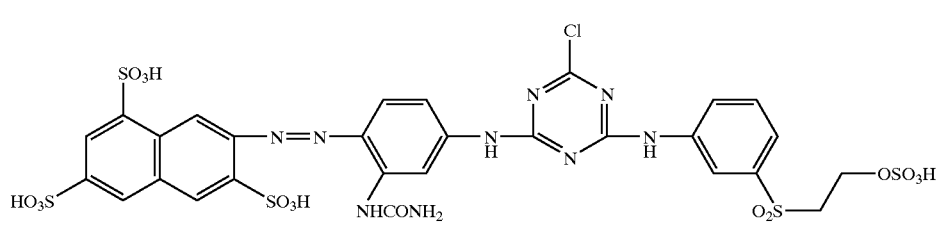

C.I. Reactive Yellow 145

In recent, more advanced methods are required to dye fibre materials with reactive dyes in view of the quality of dyed goods and of the efficiency of dying process, which needs novel reactive dyes that have a sufficient direct-dyeing property in the dyeing process and, if not fixed on fiber, can be easily washed. Accordingly, the novel reactive dyes are strongly required that also have an excellent fastness to light, laundering, etc. while satisfying the above requirements.

Therefore, an object of the present invention is to provide reactive dyes which have a high fixing capacity and a high fiber-dye bond stability and an excellent fastness property to light and water and in which a part of dyes, having been not fixed on a fiber, can be easily washed. Furthermore, the reactive dyes in accordance with the present invention exhibit a significantly higher solubility than do the well-known dyes in which two heterogeneously or homogeneously monoazo moieties are connected to each other in a backbone, thereby show a much higher reproducing property in the exhausting dyeing and continuous dyeing.

The inventors of the present writing, after having conducted extensive research and many experiments, found that novel dyes as described in the formula 1 have a good build-up capacity as well as an excellent fastness property to light and water laundering, and do not almost leave non-fixed residual components due to an excellent adsorbing/fixing properties to have an advantage in wastewater treatment, as compared with existing monochlorotriazine-based dyes and heterogeneous difunctional dyes. The dye described herein can be used in dyeing and printing fibre materials, especially cellulosic fibre material by a general fixing method. The dye has a good absorbing/fixing rate and has excellent fastness to light and wet treatments (i.e. the dye exhibits excellent color fastness when exposed to light and/or wet treatments (e.g., with water)).

SUMMARY

The fiber-reactive dye of the present invention is as defined in the formula

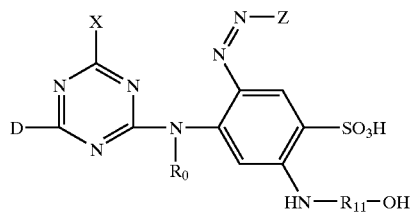
(1)

wherein, $R_{11}$ is a lower alkyl group of $C_1$–$C_4$;

D is a monoazo chromophore moiety selected from the formulas 2a, 2b, 2c, 3a and 3b defined as the below;

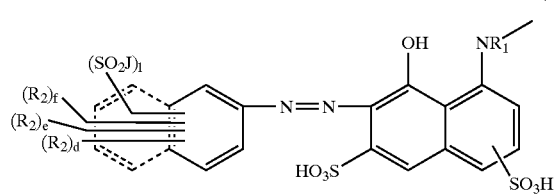
(2a)

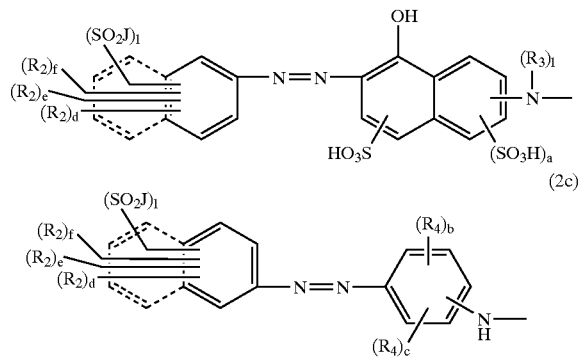
(2b)
(2c)

in the formulas 2a to 2c,
a is 0 or 1;
b is 0 or 1;
c is 0 or 1;
d is 0 or 1;
e is 0 or 1;
f is 0 or 1;
l is the number 0 or 1;
$R_1$ and $R_3$ independently of one another are each hydrogen atom or $C_1$–$C_4$ alkyl group;
$R_2$ is sulfo, $C_1$–$C_4$ alkyl, $C_1$–$C_4$ alkylalkoxy or carboxyl group;
$R_4$ is sulfo, $C_1$–$C_4$ alkyl, $C_1$–$C_4$ alkylalkoxy, —NHCONH$_2$ or —NHCOT group, wherein T is methyl, ethyl, —CH$_2$CH$_2$COOH or —CH=CHCOOH group; and
J is vinyl or CH$_2$—CH$_2$—Q group, wherein Q is a leaving group which can be eliminable by a base:

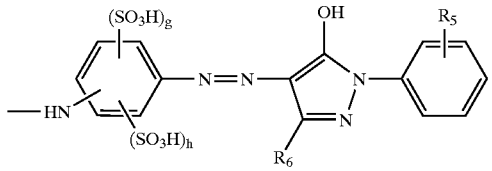
(3a)

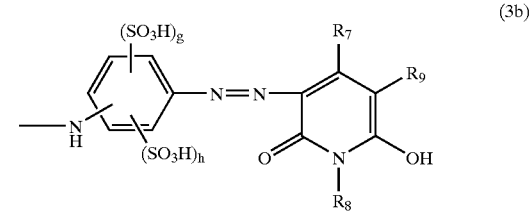
(3b)

in the formulas 3a and 3b,
g is 0 or 1;
h is 0 or 1;
$R_5$ is $C_1$–$C_4$ alkyl, $C_1$–$C_4$ alkoxy, hydroxyl, carbonyl, sulfo or —SO$_2$J group, wherein J is the same group as defined above;
$R_6$ is $C_1$–$C_4$ alkyl or carboxyl group;
$R_7$ and $R_8$ independently of one another are each $C_1$–$C_4$ alkyl group; and
$R_9$ is hydrogen atom, carboamido, sulfomethyl, methylsulfone group;
$R_0$ is hydrogen atom or $C_1$–$C_4$ alkyl group, wherein the alkyl group is substituted with halogen atom, hydroxyl, cyano, $C_1$–$C_4$ alkoxy, $C_1$–$C_4$ alkoxy carbonyl, carbonyl or sulfo group, or unsubstituted;
X is a halogen atom, hydroxyl, cyanoamine, 3-carboxypyridine-1-yl, 4-carboxypyridine-1-yl, 3-carbamoylpyridine-1-yl or an amine group optionally substituted with $C_1$–$C_4$ alkoxy or $C_1$–$C_4$ alkyl group or unsubstituted, or X is an N-heterocyclic group in which hetero atom(s) may be additionally contained; and Z is the group of the formula 4 defined as the below.

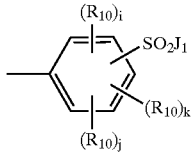
(4)

in the formula 4:
l is 0 or 1;
j is 0 or 1;
k is 0 or 1;
$R_{10}$ is sulfo, $C_1$–$C_4$ alkyl, $C_1$–$C_4$ alkoxy or carboxyl group; and
$J_1$ is vinyl or $CH_2$—$CH_2$—Q group, wherein Q is a leaving group which is eliminable by a base.

The fiber-reactive dye of the formula 1 according to the present invention has a higher reactivity, and a better fixing capacity and more excellent build-up capacity than do the existing monochlorotriazine-based compounds and vinylsulfone-based compounds.

Preferably, R is hydrogen atom, B is an ethyl group, and X is fluoride or chloride atom.

Of compounds according to the formula 1, more preferable fiber-reactive dyes are the compounds defined as in the formulas 5 to 8 below.

wherein
l is the number 0 or 1;
p is 0 or 1;
q is 0 or 1;
r is 0 or 1;
s is 0 or 1;
$R_2$ is sulfo, $C_1$–$C_4$ alkyl, $C_1$–$C_4$ alkoxy or carboxyl group;
$X_1$ is fluoride or chloride atom; and
J is vinyl or $CH_2$—$CH_2$—Q group, wherein Q is a leaving group which is eliminable by a base;

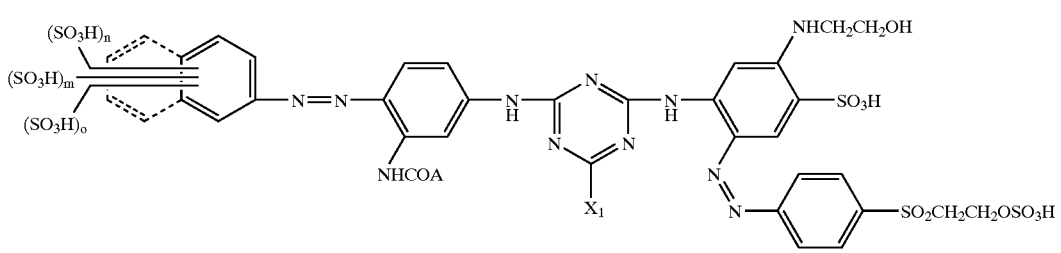
(5)

wherein
A is ammonia or $C_1$–$C_3$ alkyl group;
$X_1$ is fluoride or chloride atom; and
m is 0 or 1;
n is 0 or 1; and
o is 0 or 1;

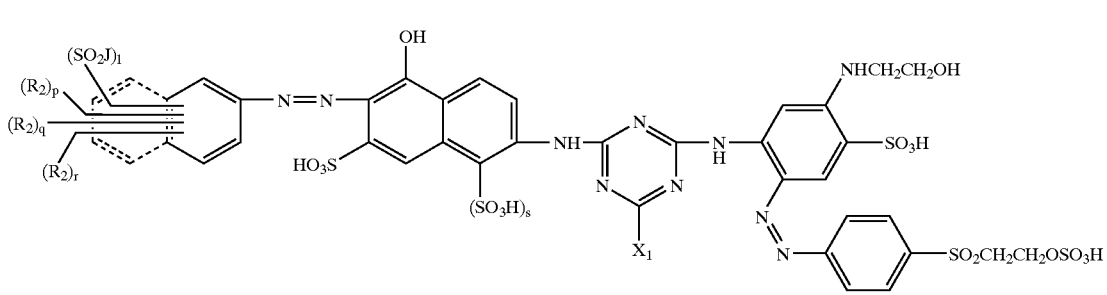
(6)

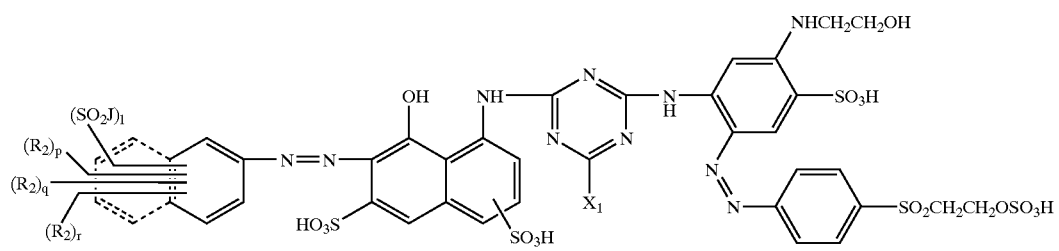
(7)

wherein
- l is the number 0 or 1;
- p is 0 or 1;
- q is 0 or 1;
- r is 0 or 1;
- s is 0 or 1;
- $R_2$ is sulfo, $C_1$–$C_4$ alkyl, $C_1$–$C_4$ alkoxy or carboxyl group;
- $X_1$ is fluoride or chloride atom; and
- J is vinyl or $CH_2$—$CH_2$—Q group, wherein Q is a leaving group which is eliminable by a base;

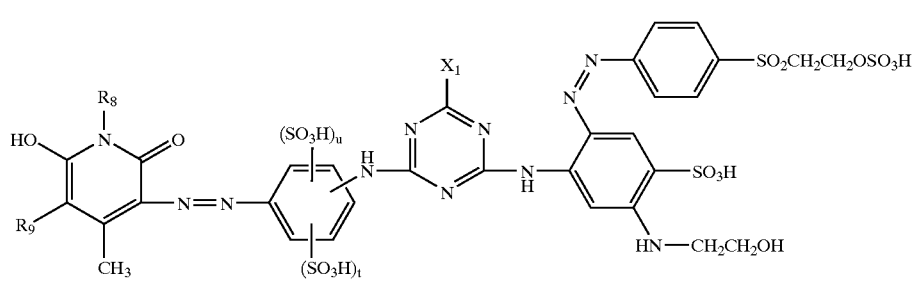
(8)

wherein
- t is 0 or 1;
- u is 0 or 1;
- $R_8$ is hydrogen atom or $C_1$–$C_4$ alkyl group, wherein the alkyl group is substituted with halogen atom, hydroxyl, cyano, $C_1$–$C_4$ alkoxy, $C_1$–$C_4$ alkoxycarbonyl, carbonyl, sulfo group, or unsubstituted;
- $R_9$ is hydrogen atom, carboamide, sulfomethyl, methyl-sulfone group; and
- $X_1$ is fluoride or chloride atom.

Methods of preparing the compounds of the formula 1 are described below. Hereinafter, $R_{11}$, D, $R_0$, X and Z in the formulas 9 to 13 are the same as in the formula 1, unless stated otherwise. For convenience of explanation, the formulas 9 to 13 are first illustrated.

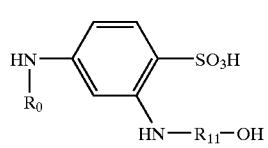
(9)

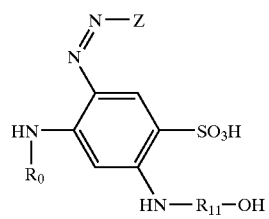
(10)

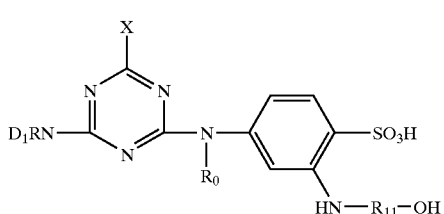
(11)

(12)

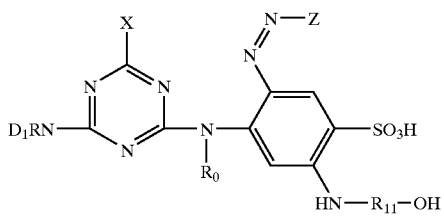
(13)

in the formulas 12 and 13, $D_1RN$ corresponds to D in the formula 1, wherein $D_1$ is a monoazo chromophore moiety; R is a substituted or unsubstituted $C_1-C_4$ alkyl group.

The compound of the formula 13, which is substantially the same as the dye defined in the formula 1, can be synthesized by one of three methods as below. It is noted that D in the formula 1 is expressed as $D_1RN$ in formula 13 for convenience of explanation.

A first method of preparing the compound of the formula 13 comprises,

A-1) the compound of the formula 11 is condensed with the compound of $HNR-D_1$, followed by being condensed with the compound of the formula 9, to yield to the compound of the formula 12; and A-2) the compound of the formula 12 is coupled with a diazonium salt derived from the compound of $H_2N-Z$ to yield the compound of the formula 13.

A second method of synthesizing the compound of the formula 13 comprises,

B-1) the compound of the formula 9 is coupled with a diazonium salt derived from the compound of $H_2N-Z$ to yield the compound of the formula 10; and B-2) the compound of the formula 11 is condensed with the compound of the formula 10, followed by being condensed with $HNR-D_1$, to yield the compound of the formula 13.

A third method of synthesizing the compound of the formula 13 comprises,

C-1) the compound of the formula 11 is condensed with the compound of the formula 9, followed by being condensed with the compound of $H_2N-Z$ to yield the compound of the formula 12; and C-2) the compound of the formula 12 is coupled with a diazonium salt derived from the compound of $H_2N-Z$ to yield the compound of the formula 13.

Diazotization/coupling reactions in the above methods can be performed by diazotizing the compound of $H_2N-Z$ with nitrous acid at $-5°-15°$ C. and pH 0.5–2, then coupling a diazonium salt thus synthesized with the compound of the formula 12 or 9 at $-5°-15°$ C. and pH 0.5–2 by an acid coupler in an aqueous medium.

Both condensation reactions in each of the above methods can be performed in an organic medium, aqueous medium, or aqueous-organic medium, and preferably performed under the presence of acid coupler in the aqueous medium. Preferable examples of said acid coupler include carbonate, bicarbonate or hydroxide of alkali metal, carbonate, bicarbonate or hydroxide of alkaline earth metal, alkali metal acetate, mixture of these, tertiary amine, etc. Preferable examples of said alkali metal and alkaline earth metal include lithium, sodium, potassium, calcium, etc. and preferable examples of said tertiary amine include pyridine, triethylamine, quinoline, etc. The first condensation reaction is performed at $-10°-40°$ C., more preferably at $0°-10°$ C. and pH 1.0–6.8.

The second condensation reaction is performed preferably under the presence of acid coupler in an aqueous medium at $10°-70°$ C. and pH 2.0–9.0, more preferably at $20°-60°$ C. and pH 2.0–8.0.

The present invention also provides a novel compound, as defined in the formula 9, which can be used as intermediate in the above methods for synthesizing the dye of the formula 1.

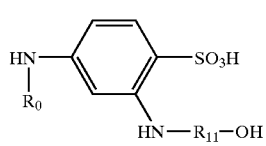

(9)

wherein $R_0$ and $R_{11}$ is the same as in the formula 1, and preferably $R_{11}$ is an ethyl group.

The compounds of the formula 9 can be synthesized by the following method: 2,4-diaminobenzene-1 sulfonic acid is acylated in No. 4 amino group of two amine groups therein by a conventional way and then No. 2 amino group is substituted with $C_1-C_4$ haloalkylalcohol, followed by the resulting reactant being hydrolyzed by conventional manners to yield the compound of the formula 9.

The present invention furthermore provides a process for dyeing or printing cellulosic fibre materials with the dye of the formula 1.

The dye of the formula 1 according to the present invention is suitable for dyeing or printing all-round cellulosic fibre materials. Examples of these cellulosic fibre materials include the naturally occurring cellulosic fibres, such as cotton, linen and hemp, and pulps and regenerated celluloses; of them, the cotton is particularly preferable. The dye of the formula 1 is also suitable for dyeing or printing cellulosic blend fibres, for example, cotton/polyester, cotton/nylon blend fibres.

For dyeing processes, the amounts in which reactive dyes, like the dye of the formula 1, are used in the dyebaths can vary according to the desired depth of shade. The dye according to the present invention can be used in the amount of 0.01 to 10% by weight, preferably 0.01 to 6% by weight, based upon the dye goods.

The dye of the formula 1 according to the present invention is especially suitable for the exhaustion method.

Dyeing by the exhaustion method is in general carried out in an aqueous medium at a liquor ration of 1:2 to 1:60, preferably 1:5 to 1:20, and a temperature of 20 to 105° C., preferably 30 to 90° C., more preferably 40 to 80° C.

The pad dyeing method is another suitable dyeing process for the present invention, wherein fabrics is generally picked-up in an aqueous solution, saline solution, salt solution, etc. Herein, pick-up is carried out at 20 to 150%, preferably 40 to 120%, more preferably 50 to 100%, based upon the weight of fibre material to be dyed. If appropriate in some cases, the aqueous solution contains a fixing alkali metal salt, and the fibre material after pick-up is treated with the fixing alkali metal salt. Preferable examples of said alkali metal salt include sodium carbonate, sodium bicarbonate, sodium hydroxide, disodium phosphate, trisodium phosphate, sodium borate, aqueous ammonia, sodium trichloroacetate, sodium silicate, or mixtures of these. Since alkali hydroxide and/or alkali carbonate is preferable, sodium hydroxide and/or sodium carbonate of them is more preferable.

Fixation can be also performed by steaming the picked-up fibre material at 100° to 120° C., particularly by action of heat, such as saturated steam. According to, so-called, cold pad-batch method, dyes are put into a padder together with alkali, then kept at a room temperature for several hours, e.g., 3 to 40 hours, to be fixed to the fibre material. After fixation, the dyeings or prints are rinsed throughout, if appropriate, by adding a dispersing agent thereto.

The dyeings and prints produced by the present invention on fibre materials have an excellent build-up capacity and levelness. Moreover, they have a high fixing capacity and the unfixed dyes can be easily removed by rinsing. Also, the difference between adsorbing and fixing capacities, i.e., the loss of soap is low. Furthermore, they have a high depth of shape, a high fibre/dye bond stability, and a good light-fastness and good wet-fastness properties, such as fastness to washing, sea water, cross-dyeing and perspiration, as well as a good fastness to pleating and fastness to ironing.

DETAILED DESCRIPTION OF PREFERRED EMBODIMENTS

Figure 1:
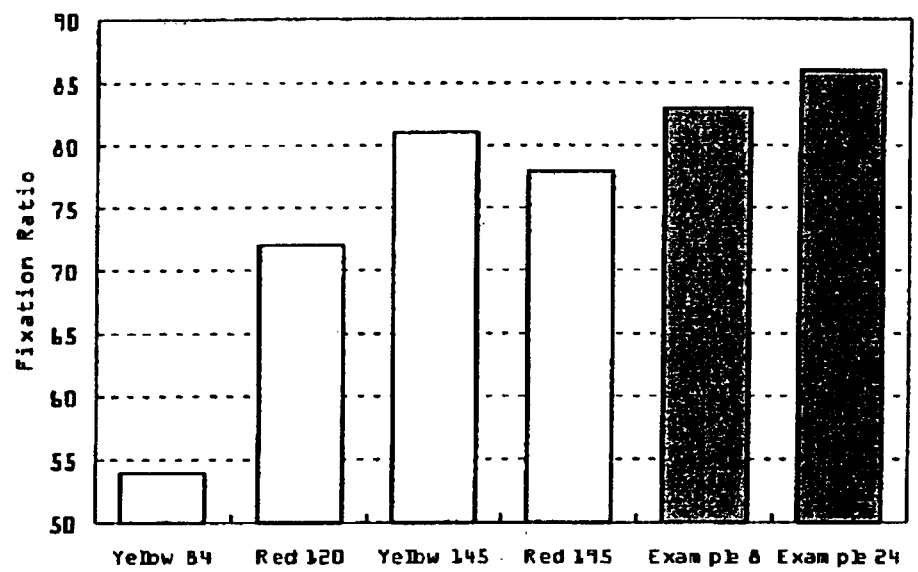
FIG. 1 is a graph of comparing the fixing rates of the dye synthesized in Example 8 according to the present invention, the dye synthesized in Example 24 according to the present invention, C.I. Reactive Red 120 dye, and C.I. Reactive Red 195 dye.

The present invention is described in more detail with reference to the following examples. However, the scope of the present invention is not limited to these.

EXAMPLE 1

4-aminobenzene-1,3-disulfonic acid was diazotized in the customary manner and then coupled with 3-ureidoaminoaniline to yield a monoazo compound. To 1000 g of an aqueous solution in which 41.54 g of the monoazo compound thus prepared was dissolved, 19.32 g of cyanuric chloride was added, followed by the condensation reaction being conducted at 5° C. and pH 5 for 3 hours. When the reaction was ended, 23.26 g of 1-amino-3-(2-hydroxyethyl)aminobenzene-4-sulfonic acid was added, followed by the condensation reaction being conducted at 30° C. and pH 5 for 3 hours. To the reaction solution, 28.13 g of diazo solution of 4-sulfatoethylsulfone-1-aminobenzene was added, followed by the coupling reaction being conducted at 10° C. and pH 5.5 for 3 hours. After non-dissolved components were removed from the resulting solution by filtering, 105.14 g of the brown compound, as depicted in the below formula, $\lambda_{max}$=421 nm, was obtained.

This compound dyed cellulosic fibres in yellow shades with a good light-fastness and washing-fastness properties. For confirmation of the fastness to washing, the below several dyeing processes were conducted.

Dyeing 1

2 g of the dye compound as obtained above was dissolved in 400 g of water. To this solution, 1500 g of a solution containing 53 g of sodium chloride per liter was added to prepare a dyebath. 100 g of a cotton fabric was introduced in the dyebath at 40° C. and, after 45 minutes, 100 g of a solution containing 16 g of sodium hydroxide and 20 g of anhydrous sodium carbonate per liter was added thereto. The dyebath was kept at 40° C. for 45 minutes. Thereafter, the dyed fabric was rinsed, soaped at the boil with a nonionic detergent for 25 minutes, rinsed again, and subsequently dried.

Dyeing 2

2 g of the dye compound as obtained above was dissolved in 400 g of water. To this solution, 1500 g of a solution containing 53 g of sodium chloride per liter was added to prepare a dyebath. 100 g of a cotton fabric was introduced in the dyebath at 35° C. and, after 20 minutes, 100 g of a solution containing 16 g of sodium hydroxide and 20 g of anhydrous sodium carbonate per liter was added thereto. The dyebath was kept at 35° C. for 15 minutes, then heated to 60° C. in the course of 20 minutes and kept at this temperature for a further 35 minutes. Thereafter, the dyed fabric was rinsed, soaped at the boil with a nonionic detergent for 25 minutes, rinsed again, and subsequently dried.

Printing 3 g of the dye compound as obtained above was sprinkled, while stirring rapidly, into 100 g of a stock thickener comprising 50 g of sodium alginate thickener, 27.8 g of water, 20 g of urea and 1.2 g of sodium m-nitrobenzenesulfonate. A cotton fabric was printed with the printing paste thus prepared. The printed fabric was steamed at 102° C. in saturated steam for 2 minutes and then rinsed, if appropriate soaped at the boil and rinsed again, and subsequently dried.

EXAMPLE 2

4-aminobenzene-1,3-disulfonic acid was diazotized in the customary manner and then coupled with 3-ureidoaminoaniline to yield a monoazo compound. To 1000 g of an aqueous solution in which 41.54 g of the monoazo compound prepared thus was dissolved, 13.91 g of cyanuric fluoride was added, followed by the condensation reaction being conducted at 0° C. and pH 5 for 3 hours. When the reaction was ended, 23.26 g of 1-amino-3(2-

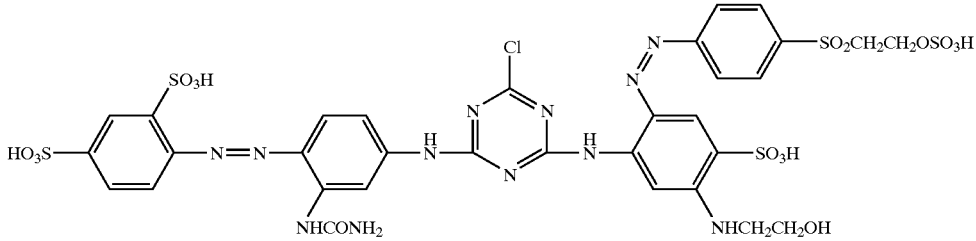

hydroxyethyl)aminobenzene-4-sulfonic acid was added, followed by the condensation reaction being conducted at 30° C. and pH 5 for 3 hours. To the reaction solution, a diazonium salt solution containing 28.13 g of 4-sulfatoethylsulfone-1-aminobenzene was added, followed by the coupling reaction being conducted at 10° C. and pH 5.5 for 3 hours. After non-dissolved components were removed from the resulting solution by filtering, 103.5 g of the brown compound, as depicted in the below formula, $\lambda_{max}$=420 nm, was obtained.

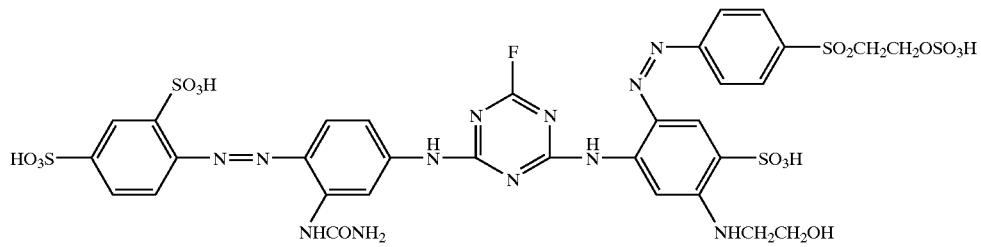

This compound dyed cellulosic fibres in yellow shades with a good light-fastness and washing-fastness properties. For confirmation of the fastness to washing, the dyeing processes were conducted in the same manner as in EXAMPLE 1.

EXAMPLE 3

19.32 g of cyanuric chloride was suspended in an aqueous solution below 0° C. for 30 minutes and a solution containing 23.93 g of 6-amino-1-naphthol-3-sulfonic acid was added thereto. The resulting solution was kept at pH 3 and 5° C. until the condensation reaction was completed.

30.31 g of 2-amino-naphthol-1,5-disulfonic acid was diazotized in the customary manner, then added to the above reaction solution to conduct the additional condensation reaction at pH 8 and 10° C.

To the resulting solution, 23.26 g of 1-amino-3-(N-hydroxyethyl)aminobenzene-4-sulfonic acid was added, and the reaction solution was kept at pH 5 and 50° C. for 3 hours to complete the reaction, followed by a diazonium salt corresponding to 28.13 g of 4-sulfatoethylsulfon-1-aminobenzene being added thereto. When the reaction was ended at pH 7 and 10° C., non-solved components were removed by filtering and then the reactant was dried. Subsequently, a deep brown compound of the below formula ($\lambda_{max}$=480 nm) was obtained in an amount of 119 g.

This compound dyed cellulosic fibres in scarlet shades with a good light-fastness and washing-fastness properties. For confirmation of the fastness to washing, the dyeing processes were conducted in the same manner as in EXAMPLE 1.

EXAMPLE 4

28.13 g of 4-sulfatoethylsulfone-1-aminobenzen was diazotized in the customary manner, and the diazonium salt solution thus prepared was added to a solution in which 23.26 g of 1-amino-3-(N-hydroxyethyl)aminobenzen-4-sulfonic acid was dissolved as a coupling component to conduct the coupling reaction. To 100 g of the solution in which 52.46 g of the monoazo compound obtained from the above reaction was contained, 19.32 g of cyanuric chloride was added, then kept at pH 5 and 5° C. for 3 hours. When the reaction was ended, the aqueous solution containing 31.93 g of 8-amino-1-naphthol-3,6-disulfonic acid was added to the reaction solution, then kept at pH 5 and 30° C. for 3 hours. To this solution, the diazonium salt solution corresponding to 30.31 g of 2-amino-naphthalene-1,5-disulfonic acid was added, then kept at pH 5.5 and 10° C. for 3 hours to complete the reaction. Non-dissolved component were removed from the reaction solution by filtering and then the resultant was dried. Subsequently, a dark red compound of the below formula ($\lambda_{max}$=514 nm) was obtained in an amount of 126.96 g.

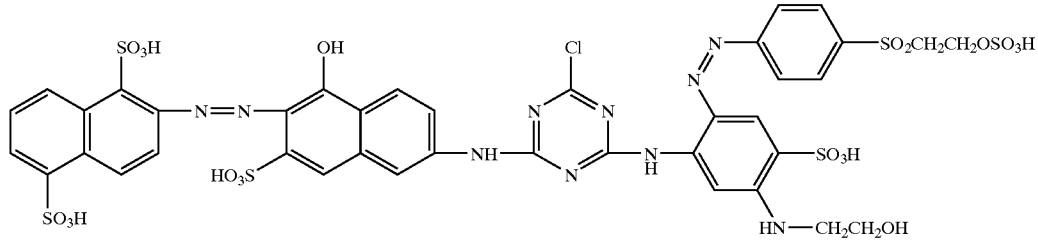

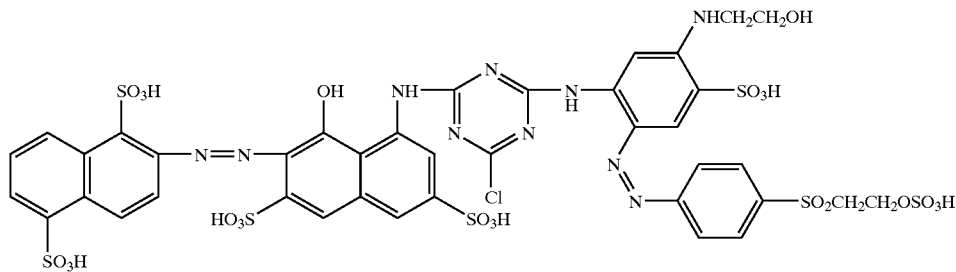

This compound dyed cellulosic fibres in deep red shades with a good light-fastness and washing-fastness properties. For confirmation of the fastness to washing, the dyeing processes were conducted in the same manner as in EXAMPLE 1.

EXAMPLES 5 TO 24

Similarly to the above EXAMPLES, the compounds ($R_{11}$=$CH_2CH_2$) as described in TABLE 1 were synthesized. The methods for synthesizing these compounds can be easily understood from the above EXAMPLES and their chemical structures by the persons skilled in the art, without detailed description. These compounds were tested in the same manner as in EXAMPLE 1.

From the testing results, these compounds were to confirmed to be dyes which have a very good fiber-reactive property, and can dye or print cellulosic fibre materials by the fixing method, generally used in the field of fiber-reactive dye, and also have a good adsorbing/fixing rate and a very excellent fastness to light and wet treatment.

TABLE 1

| EXAMPLE | D (monoazo chromphore) | X | Z | Color of dyed materials |
|---|---|---|---|---|
| 5 | (pyridone azo structure with $CH_2CH_3$, HO, $HO_3S$—$H_2C$, $CH_3$, $HO_3S$, NH—) | Cl | phenyl-$SO_2CH_2CH_2OSO_3H$ with CH$_3$ | Yellow |
| 6 | (pyridone azo structure with $CH_2CH_3$, HO, $H_2N$—C(O), $CH_3$, $HO_3S$, NH—) | Cl | phenyl-$SO_2CH_2CH_2OSO_3H$ with CH$_3$ | Yellow |
| 7 | (pyrazole azo structure with $H_3C$, COOH, $SO_3H$, OH, $HO_3S$, NH—) | Cl | phenyl-$SO_2CH_2CH_2OSO_3H$ with CH$_3$ | Yellow |
| 8 | (naphthalene azo structure with $SO_3H$, $HO_3S$, $SO_3H$, NH—, $NHCONH_2$) | Cl | meta-substituted phenyl-$SO_2CH_2CH_2OSO_3H$ with CH$_3$ | Yellow |

TABLE 1-continued

| EXAMPLE | D (monoazo chromphore) | X | Z | Color of dyed materials |
|---|---|---|---|---|
| 9 | Naphthalene with SO₃H, HO₃S, SO₃H, –N=N–phenyl(NHCONH₂)–NH– | F | p-tolyl–SO₂CH₂CH₂OSO₃H | Yellow |
| 10 | Naphthalene with SO₃H, SO₃H, –N=N–phenyl(NHCOCH₃)–NH– | N-methylmorpholine | HO₃S, methylphenyl–SO₂CH₂CH₂O | Yellow |
| 11 | Benzene with SO₃H, HO₃S, –N=N–phenyl(NHCONH₂)–NH– | p-(SO₂CH₂CH₂OSO₃H)phenyl–NH– | m-tolyl–SO₂CH₂CH₂OSO₃H | Yellow |
| 12 | O₂N–phenyl(SO₃H)–N=N–phenyl(HO₃S)(NHCOCH₃)–N=N–phenyl–NH– | Cl | p-tolyl–SO₂CH₂CH₂OSO₃H | Yellow |
| 13 | Phenyl(SO₃H)–N=N–naphthyl(OH)(HO₃S)–NH– | Cl | HO₃S, methylphenyl–SO₂CH₂CH₂OSO₃H | Orange |
| 14 | Phenyl(SO₃H)(HO₃S)–N=N–naphthyl(OH)(HO₃S)–NH– | Cl | m-tolyl–SO₂CH₂CH₂OSO₃H | Orange |
| 15 | Naphthyl(SO₃H)(SO₃H)–N=N–naphthyl(OH)(HO₃S)–NH– | Cl | m-tolyl–SO₂CH₂CH₂OSO₃H | Orange |

TABLE 1-continued

| EXAMPLE | D (monoazo chromphore) | X | Z | Color of dyed materials |
|---|---|---|---|---|
| 16 | 2,5-disulfophenyl-azo-1-hydroxy-6-dimethylamino-3-sulfo-naphthalene | F | 4-methylphenyl-SO$_2$CH$_2$CH$_2$OSO$_3$H | Orange |
| 17 | 1-sulfo-5-sulfo-naphth-2-yl-azo-1-hydroxy-6-methylamino-5-sulfo-3-sulfo-naphthalene | F | 4-methylphenyl-SO$_2$CH$_2$CH$_2$OSO$_3$H | Orange |
| 18 | 4-(HO$_3$SOCH$_2$CH$_2$CO$_2$S)phenyl-azo-1-hydroxy-6-methylamino-3-sulfo-5-sulfo-naphthalene | F | 3-methylphenyl-SO$_2$CH$_2$CH$_2$OSO$_3$H | Orange |
| 19 | 4-methoxy-2-sulfo-phenyl-azo-1-hydroxy-6-methylamino-3-sulfo-naphthalene | N-methylmorpholino | 2-methyl-3-sulfo-5-(SO$_2$CH$_2$CH$_2$OSO$_3$H)phenyl | Orange |
| 20 | 4-(HO$_3$SOCH$_2$CH$_2$CO$_2$S)phenyl-azo-1-hydroxy-8-methylamino-3,6-disulfo-naphthalene | Cl | 4-methylphenyl-SO$_2$CH$_2$CH$_2$OSO$_3$H | Scarlet |
| 21 | 1-sulfo-5-sulfo-naphth-2-yl-azo-1-hydroxy-8-methylamino-3,6-disulfo-naphthalene | Cl | 4-methylphenyl-SO$_2$CH$_2$CH$_2$OSO$_3$H | Scarlet |
| 22 | 1-sulfo-5-sulfo-naphth-2-yl-azo-1-hydroxy-8-methylamino-3-sulfo-6-sulfo-naphthalene | F | 3-methylphenyl-SO$_2$CH$_2$CH$_2$OSO$_3$H | Scarlet |

TABLE 1-continued

| EX-AMPLE | D (monoazo chromphore) | X | Z | Color of dyed materials |
|---|---|---|---|---|
| 23 | | F | (m-tolyl)-SO₂CH₂CH₂OSO₃H | Scarlet |
| 24 | | Cl | (p-tolyl)-SO₂CH₂CH₂OSO₃H | Scarlet |

COMPARATIVE EXAMPLES 1 & 2

The relative extent of dyeing was measured for cotton fabrics dyed with the dyes synthesized in EXAMPELS 8 and 24, C.I. Reactive Yellow 84 dye, C.I. Reactive Red 120 dye, C.I. Reactive Yellow 145 dye and C.I. Reactive Red 195, respectively, in the same manner as in DYEING-1 in EXAMPLE 1. For this, the relative dyeing intensity was measured using a color difference meter (Gretag Macbeth LLC.), and the fixing rates before dyeing and after dyeing were measured using a UV spectrometer (Agilent Technologies Inc.). The results are described in FIGS. 1 and 2, respectively.

Figure 2:
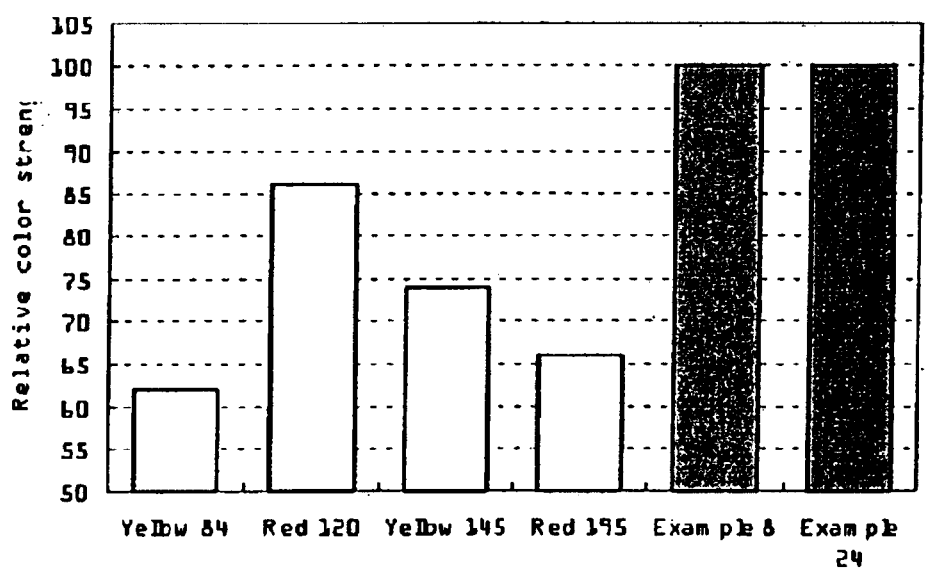
FIG. 2 is a graph of comparing the relative dyeing intensities of the dye synthesized in Example 8 according to the present invention, the dye synthesized in Example 24 according to the present invention, C.I. Reactive Red 120 dye, and C.I. Reactive Red 195 dye.

As seen from FIGS. 1 and 2, the dyes of EXAMPLES 8 and 24 according to the present invention were confirmed to exhibit a better fixing rate and relative dyeing intensity than do C.I. Reactive Yellow 84 dye, C.I. Reactive Red 120 dye, C.I. Reactive Yellow 145 dye and C.I. Reactive Red 195 dye.

COMPARATIVE EXAMPLE 3

Each solubility of the compound of the below formula 14, being a well-known dye in the relevant prior art, and the dye produced in EXAMPLE 24 was measured under the conditions of exhaustion dyeing and continuous dyeing, respectively. Specifically, the solubility in the exhaustion dyeing condition was measured as a maximum concentration of both dyes soluble in a solution containing sodium carbonate of 20 g/L and sodium sulfate of 50 g/L at 60° C. for 30 minutes. The solubility in the continuous dyeing condition was measured as a maximum concentration of both dyes soluble in a solution containing 25% sodium hydroxide of 26 mL and sodium sulfate of 30 g/L at 30° C. for 120 minutes. The results are described in FIG. 3, respectively.

(14)

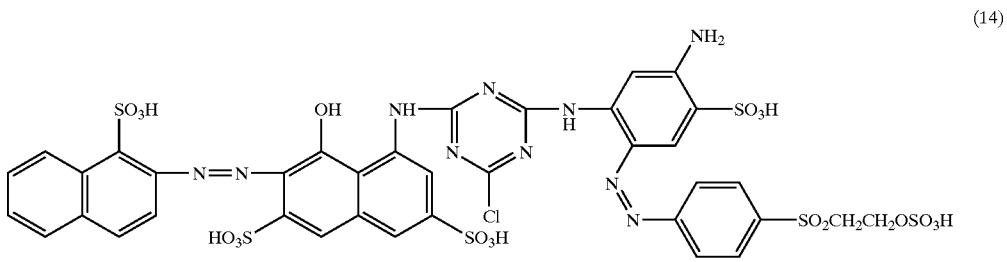

Figure 3:
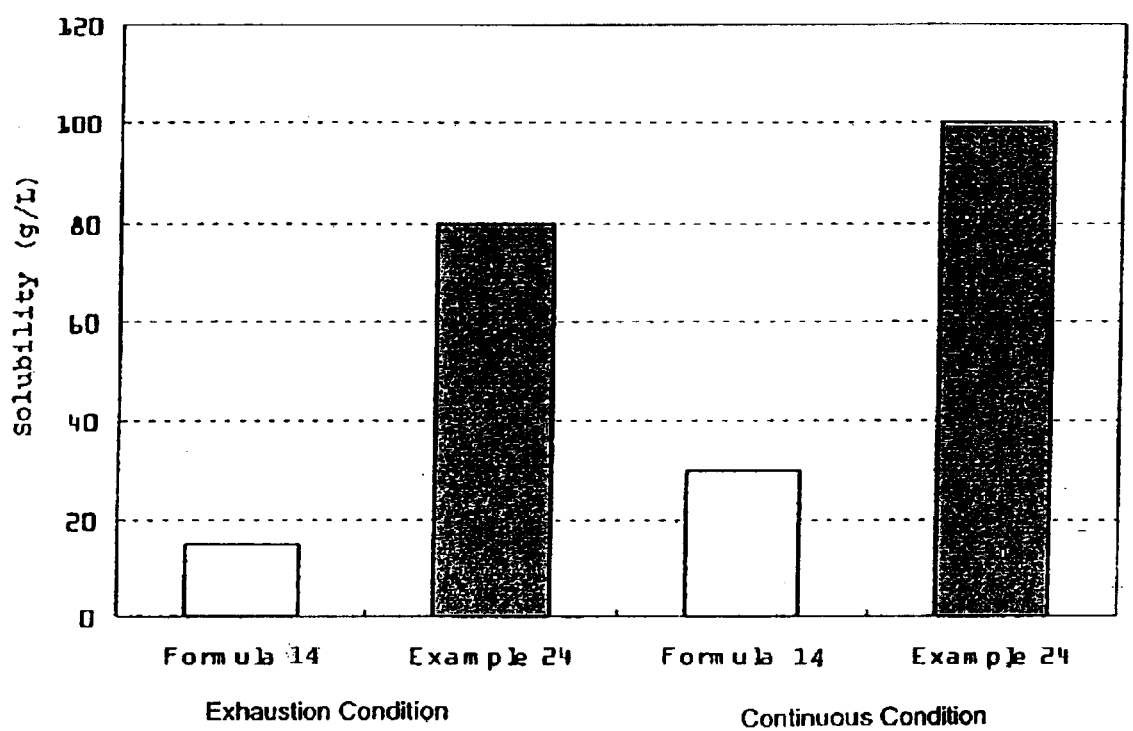
FIG. 3 is a graph of comparing the solubilities of the dye of prior art (refer to the formula 14 as mentioned later) and the dye of EXAMPLE 24 in the conditions of exhaustion dyeing and continuous dyeing.

As seen from FIG. 3, the dye of EXAMPLE 24 according to the present invention was confirmed to exhibit a significant solubility than do the dye compound of the formula 14 as a known dye, in both exhaustion dyeing and continuous dyeing conditions.

The invention being thus described, it will be obvious that it is susceptible to obvious modifications and variations. Such variations are not to be regarded as a departure from the spirit and scope of the invention, and all such modifications as would be obvious to one skilled in the art were intended to be included within the scope of the following claims.

The Applicant reserves the right to claim or disclaim now or in the future any feature, combination of features, or subcombination of features that is disclosed herein.

All of the numerical and quantitative measurements set forth in this application (including in the description, claims, abstract, drawings, and any appendices) are approximations.

The invention illustratively disclosed or claimed herein suitably may be practiced in the absence of any element which is not specifically disclosed or claimed herein. Thus, the invention may comprise, consist of, or consist essentially of the elements disclosed or claimed herein.

The following claims are entitled to the broadest possible scope consistent with this application. The claims shall not necessarily be limited to the preferred embodiments or to the embodiments shown in the examples.

This patent application claims Convention priority to Korean Patent Application No. 10-2002-0030331 (filed 30 May 2002), to Korean Patent Application No. 10-2002-0030333 (filed 30 May 2002), and to Korean Patent Application No. 10-2002-0030398 (filed 30 May 2002). The entire contents of Korean Patent Application Nos. 10 2002-0030331, 10-2002-0030333, and 10-2002-0030398 are expressly incorporated herein by this reference.

All patents, prior filed patent applications, and any other documents and printed matter cited or referred to in this application are incorporated in their entirety herein by this reference.

What is claimed is:

1. A fiber-reactive dye as defined in formula 1 below:

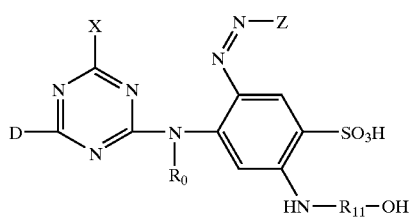

(1)

wherein, $R_{11}$ is a lower alkyl group consisting of $C_1$–$C_4$;

D is a monoazo chromophore moiety as defined below in formula 2a, 2b, 2c, 3a, or 3b:

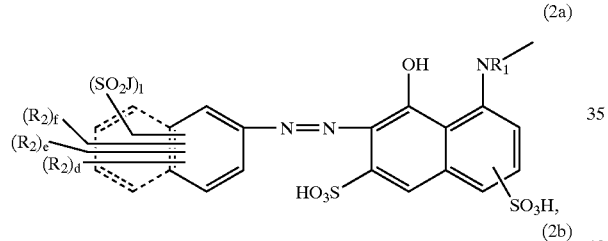

(2a)

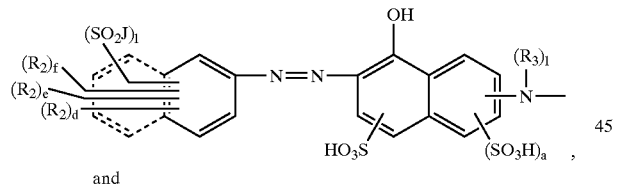

(2b)

and

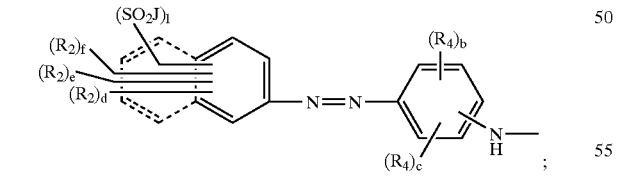

(2c)

wherein in the formulas 2a to 2c,
a is 0 or 1;
b is 0 or 1;
c is 0 or 1;
d is 0 or 1;
e is 0 or 1;
f is 0 or 1;
l is 0 or 1;
$R_1$ and $R_3$ independently of one another are each a hydrogen atom or a $C_1$–$C_4$ alkyl group;

each $R_2$ is independently a sulfo, $C_1$–$C_4$ alkyl, $C_1$–$C_4$ alkylalkoxy, or carboxyl group;

each $R_4$ is independently a sulfo, $C_1$–$C_4$ alkyl, $C_1$–$C_4$ alkylalkoxy, —NHCONH$_2$, or a —NHCOT group, wherein T is methyl, ethyl, —CH$_2$CH$_2$COOH, or a —CH=CHCOOH group; and J is vinyl or a CH$_2$—CH$_2$—Q group, wherein Q is a leaving group which can be eliminated by a base as defined in the formula 3a or 3b below:

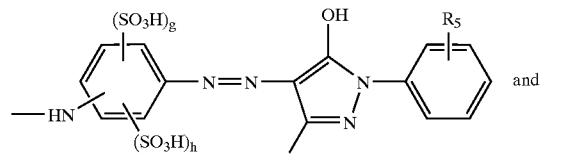

(3a)

and

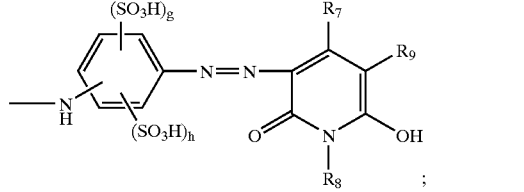

(3b)

wherein in the formulas 3a and 3b,
g is 0 or 1;
h is 0 or 1;
$R_5$ is a $C_1$–$C_4$ alkyl, $C_1$–$C_4$ alkoxy, hydroxyl, carbonyl, sulfo, or —SO$_2$J group, wherein J is defined above;
$R_6$ is a $C_1$–$C_4$ alkyl or carboxyl group;
$R_7$ and $R_8$ independently of one another are each a $C_1$–$C_4$ alkyl group; and
$R_9$ is a hydrogen atom, or a carboamido, sulfomethyl, or methylsulfone group;

$R_0$ is a hydrogen atom or a $C_1$–$C_4$ alkyl group, wherein the alkyl group is optionally substituted with a halogen atom, or $R_0$ is a hydroxyl, cyano, $C_1$–$C_4$ alkoxy, $C_1$–$C_4$ alkoxy carbonyl, carbonyl, or sulfo group;

X is a halogen atom or a hydroxyl, cyanoamine, 3-carboxypyridine-1-yl, 4-carboxypyridine-1-yl, or 3-carbamoylpyridine-1-yl group, or X is an amine group optionally substituted with a $C_1$–$C_4$ alkoxy or $C_1$–$C_4$ alkyl group, or X is an N-heterocyclic group in which hetero atom(s) may be additionally contained; and Z is a group as defined in formula 4 below:

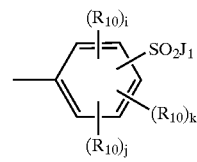

(4)

wherein in the formula 4:
i is 0 or 1;
j is 0 or 1;
k is 0 or 1;
each $R_{10}$ is independently a sulfo, $C_1$–$C_4$ alkyl, $C_1$–$C_4$ alkoxy, or carboxyl group; and
$J_1$ is vinyl or a CH$_2$—CH$_2$—Q group, wherein Q is defined above.

2. The dye according to claim 1, wherein $R_0$ is a hydrogen atom, $R_{11}$ is an ethyl group, and X is a fluoride or chloride atom.

3. The dye according to claim 1, wherein the dye is one of the compounds defined in formulas 5 to 8 below:

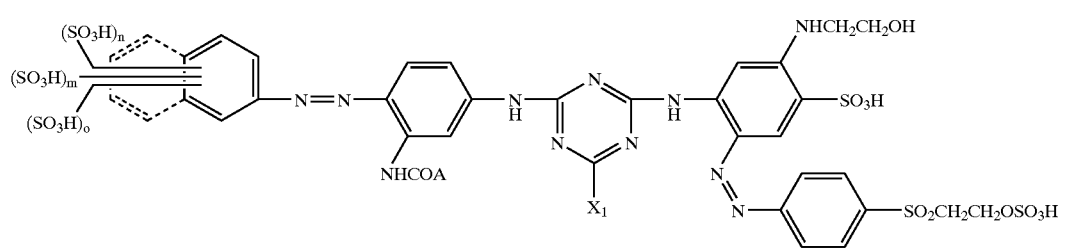

wherein in the formula 5:
A is ammonia or a $C_1$–$C_3$ alkyl group;
$X_1$ is a fluoride or chloride atom;
m is 0 to 1;
n is 0 or 1; and
o is 0 or 1;

wherein in the formula 7:
l is 0 or 1;
p is 0 or 1;
q is 0 or 1;
r is 0 or 1;
s is 0 or 1;
each $R_2$ is independently a sulfo, $C_1$–$C_4$ alkyl, $C_1$–$C_4$ alkoxy, or carboxyl group;
$X_1$ is a fluoride or a chloride atom; and
J is vinyl or a $CH_2$—$CH_2$—Q group, wherein Q is defined in claim 1;

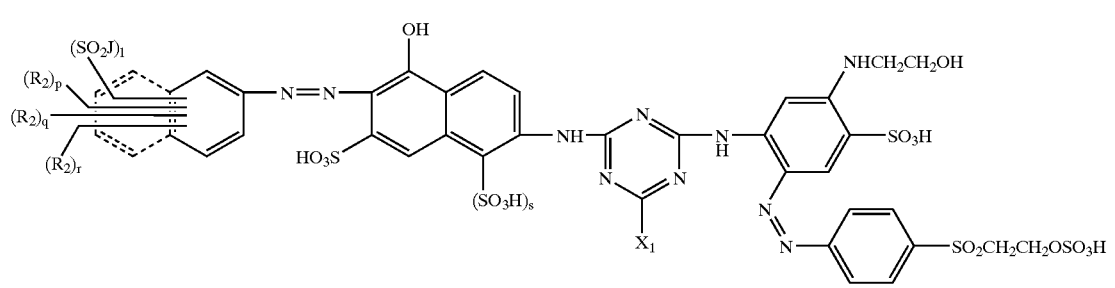

wherein in the formula 6:
l is 0 or 1;
p is 0 or 1;
q is 0 or 1;
r is 0 or 1;
s is 0 or 1;
each $R_2$ is independently a sulfo, $C_1$–$C_4$ alkyl, $C_1$–$C_4$ alkoxy or carboxyl group;
$X_1$ is a fluoride or chloride atom; and
J is vinyl or a $CH_2$—$CH_2$—Q group, wherein Q is defined in claim 1;

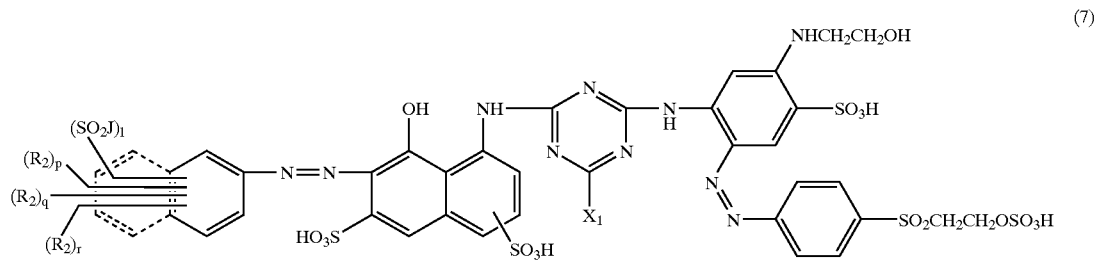

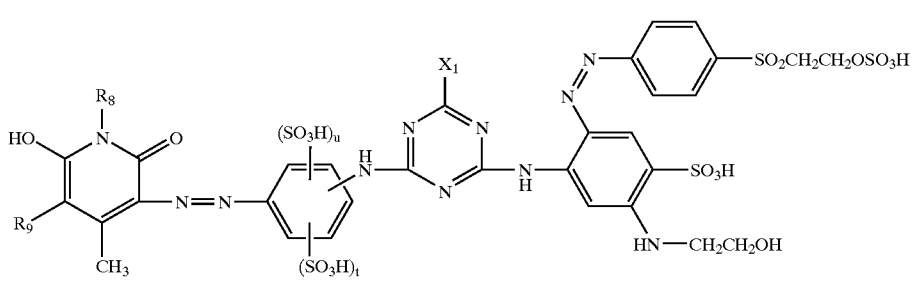

wherein in the formula 8:

t is 0 or 1;

u is 0 or 1;

$R_8$ is a hydrogen atom or a $C_1$–$C_4$ alkyl group, wherein the alkyl group is optionally substituted with a halogen atom, or a hydroxyl, cyano, $C_1$–$C_4$ alkoxy, $C_1$–$C_4$ alkoxycarbonyl, carbonyl, or sulfo group;

$R_9$ is a hydrogen atom, or a carboamide, sulfomethyl, or methylsulfone group; and $X_1$ is a fluoride or chloride atom.

4. A method of preparing the dye of the formula 1 as claimed in claim 1, wherein the method is one of Methods (A), (B), and (C) as defined below:

Method (A) comprises the following steps:
  A-1) a compound defined in formula 11 below is condensed with a compound defined by formula HNR-$D_1$, followed by being condensed with a compound defined in formula 9 below, to yield a compound defined in formula 12 below; and
  A-2) the compound defined in the formula 12 is coupled with a diazonium salt derived from a compound defined in formula $H_2N$-Z to yield a compound defined in formula 13 below;

Method (B) comprises the following steps:
  B-1) a compound defined in formula 9 below is coupled with a diazonium salt derived from the compound of the formula $H_2N$-Z to yield a compound defined in formula 10 below; and
  B-2) the compound defined in the formula 11 is condensed with the compound defined in the formula 10, followed by being condensed with HNR-$D_1$, to yield the compound defined in the formula 13;

Method (C) comprises the following steps:
  C-1) the compound defined in the formula 11 is condensed with the compound defined in the formula 9, followed by being condensed with the compound defined in the formula $H_2N$-Z to yield the compound defined in the formula 12; and
  C-2) the compound defined in the formula 12 is coupled with a diazonium salt derived from the compound defined in the formula $H_2N$-Z to yield the compound defined in the formula 13;

wherein the formula 9 is:

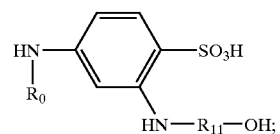

wherein the formula 10 is:

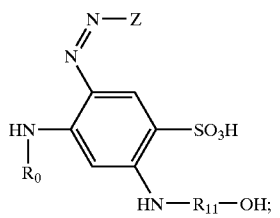

wherein the formula 11 is:

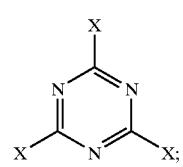

wherein the formula 12 is:

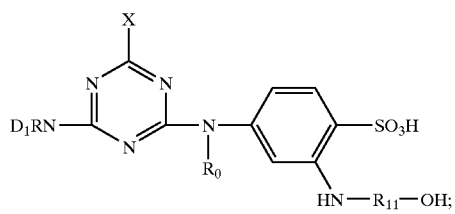

wherein the formula 13 is:

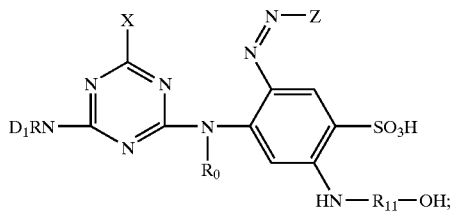

(13)

wherein $R_{11}$, D, $R_0$, X and Z are defined in claim 1; wherein $D_1$ is a monoazo chromophore moiety; wherein R is a substituted or unsubstituted $C_1$–$C_4$ alkyl group; and wherein the $D_1RN$ in the formula 13 corresponds to D in the formula 1 in claim 1.

5. A compound defined in formula 9 below:

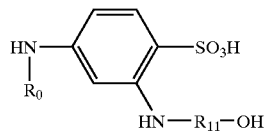

(9)

wherein $R_0$ is a hydrogen atom or a $C_1$–$C_4$ alkyl group, wherein the alkyl group is optionally substituted with a halogen atom, or $R_0$ is a hydroxyl, cyano, $C_1$–$C_4$ alkoxy, $C_1$–$C_4$ alkoxy carbonyl, carbonyl, or sulfo group; and wherein $R_{11}$ is a lower alkyl group of $C_1$–$C_4$.

6. The compound according to claim 5, wherein $R_{11}$ is an ethyl group.

7. A method of preparing the compound as claimed in claim 6, wherein the amino group of No. 4 in 2,4-diaminobenzene-1 sulfonic acid is acylated, and the amino group of No. 2 is substituted with $C_1$–$C_4$ haloalkylalcohol, followed by being hydrolyzed.

8. A process for dyeing and printing cellulosic fibre materials, which comprises treating the fibre materials with the dye defined in the formula 1 as claimed in claim 1.

\* \* \* \* \*